United States Patent
Joshi et al.

(10) Patent No.: US 7,432,240 B2
(45) Date of Patent: Oct. 7, 2008

(54) FUMARIC ACID AMIDES

(75) Inventors: Rajendra Kumar Joshi, Zurich (CH); Hans-Peter Strebel, Lucerne (CH)

(73) Assignee: Biogen Idec International GmbH, Zug (CH)

( * ) Notice: Subject to any disclaimer, the term of this patent is extended or adjusted under 35 U.S.C. 154(b) by 0 days.

(21) Appl. No.: 11/421,083

(22) Filed: May 31, 2006

(65) Prior Publication Data

US 2006/0205659 A1    Sep. 14, 2006

Related U.S. Application Data

(62) Division of application No. 10/433,295, filed as application No. PCT/EP02/00107 on Jan. 8, 2002, now Pat. No. 7,157,423.

(30) Foreign Application Priority Data

Jan. 12, 2001 (DE) .................. 101 01 307
Jul. 6, 2001 (DE) .................. 101 33 004

(51) Int. Cl.
*A61K 38/00*  (2006.01)
*A61K 38/02*  (2006.01)
*C07K 2/00*  (2006.01)
*C07K 1/107*  (2006.01)

(52) U.S. Cl. ............... 514/2; 530/300; 530/345

(58) Field of Classification Search ........... None
See application file for complete search history.

(56) References Cited

U.S. PATENT DOCUMENTS

| | | | |
|---|---|---|---|
| 2,993,837 A | 7/1961 | Millar et al. | |
| 3,832,287 A | 8/1974 | Gale et al. | |
| 4,515,974 A | 5/1985 | Zecher et al. | |
| 4,746,668 A | 5/1988 | Sato et al. | |
| 4,851,439 A | 7/1989 | Speiser et al. | |
| 4,959,389 A | 9/1990 | Speiser et al. | |
| 5,149,695 A | 9/1992 | Speiser et al. | |
| 5,214,196 A | 5/1993 | Blank | |
| 5,242,905 A | 9/1993 | Blank | |
| 5,350,741 A * | 9/1994 | Takada | 514/3 |
| 5,359,128 A | 10/1994 | Blank | |
| 5,424,332 A | 6/1995 | Speiser et al. | |
| 5,451,667 A | 9/1995 | Speiser et al. | |
| 5,538,968 A | 7/1996 | Chiesi et al. | |
| 5,548,059 A | 8/1996 | Bayley et al. | |
| 5,569,742 A * | 10/1996 | Kirby et al. | 530/317 |
| 5,589,504 A | 12/1996 | Dannenberg et al. | |
| 5,763,408 A | 6/1998 | Nishikawa et al. | |
| 5,972,363 A | 10/1999 | Clikeman et al. | |
| 6,277,882 B1 | 8/2001 | Joshi et al. | |
| 6,355,676 B1 | 3/2002 | Joshi et al. | |
| 6,359,003 B1 | 3/2002 | Joshi et al. | |
| 6,436,992 B1 | 8/2002 | Joshi et al. | |
| 6,509,376 B1 | 1/2003 | Joshi et al. | |
| 6,858,750 B2 | 2/2005 | Joshi et al. | |

FOREIGN PATENT DOCUMENTS

| | | |
|---|---|---|
| AU | 9921593 A * | 10/1999 |
| CA | 2248955 | 11/1998 |
| DE | 25 30 372 | 1/1977 |
| DE | 26 21 214 | 11/1977 |
| DE | 38 34 794 | 4/1990 |
| EP | 103 274 A2 | 3/1984 |
| GB | 1 216 699 | 12/1970 |
| GB | 1 422 726 | 1/1976 |
| WO | WO 89/01930 | 3/1989 |
| WO | WO 94/28883 | 12/1994 |
| WO | WO 95/25102 | 9/1995 |
| WO | WO 96/02244 | 2/1996 |
| WO | WO 96/27369 | 9/1996 |
| WO | WO 97/48400 | 12/1997 |
| WO | WO 98/04290 | 2/1998 |
| WO | WO 98/27970 | 7/1998 |

(Continued)

OTHER PUBLICATIONS

R. Andruszkiewicz et al. J. Med. Chem. (1990) 33(1), pp. 132-135.*

(Continued)

*Primary Examiner*—Andrew D Kosar
(74) *Attorney, Agent, or Firm*—Finnegan, Henderson, Farabow, Garrett & Dunner, LLP

(57) ABSTRACT

Fumaric acid amides of the general formula (I)

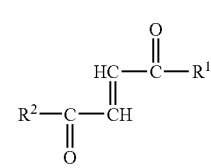

(I)

wherein $R^1$ represents $OR^3$ or a D- or L-amino acid radical —NH—$CHR^4$—COOH bonded via an amide bond, wherein $R^3$ is hydrogen, a straight-chained or branched, optionally substituted $C_{1-24}$ alkyl radical, a phenyl radical or $C_{6-10}$ aralkyl radical and $R^4$ is a side chain of a natural or synthetic amino acid and $R^2$ represents a D- or L-amino acid radical —NH—$CHR^5$—COOH bonded via an amide bond or a peptide radical comprising 2 to 100 amino acids bonded via an amide bond, wherein $R^5$ is a side chain of a natural or synthetic amino acid, are used for preparing a drug (1) for the therapy of an autoimmune disease; (2) for use in transplantation medicine; (3) for the therapy of mitochondrial diseases; or (4) for the therapy of NF-kappaB mediated diseases.

12 Claims, No Drawings

FOREIGN PATENT DOCUMENTS

| | | |
|---|---|---|
| WO | WO 98/52549 | 11/1998 |
| WO | WO 99/21565 | 5/1999 |
| WO | WO 2005/023241 | 3/2005 |

OTHER PUBLICATIONS

Aiache, J. et al., J. Pharm. Biomed. Anal 8(6): 499-506 (1990).
Altmeyer, P. et al., "Systemische Therapie der Psoriasis", T & E Derm. Jg., vol. 27, pp. 380-382, 384, 1997.
Amamoto, T. et al. "Effect of E-64, Thiol Protease Inhibitor on the Secondary Anti-SRBC Response In-Vitro", Microbiol. Immunol., vol. 28(1), pp. 85-97, 1984.
Bacharach-Buhles, M. et al., "Fumaric Acid Esters (FAEs) Suppress CD-15-and ODP 4-positive Cells in Psoriasis", Acta. Derm. Venerol., suppl. 186, pp. 79-82, 1994.
Barrett, A. J. at al., "L-trans-Epoxysuccinyl-leucylmido (4-guanidino) butane and its analogues as inhibitors of cysteine proteinases including cathepains B,H, and L", Biochem. J., vol. 201, pp. 189-198, 1982.
Bayard, W. et al., "Peroral long term treatment of psoriasis using fumaric acid derivatives", Der Hautarzt, vol. 38(5), pp. 279-285, Medline Abstract, 1987.
Bellier, B. et al., "Replacement of Glycine with Dicarbonyl and Related Moieties in Analogues of the C-Terminal Pentapeptide of Cholecystokinin:CCK4Agonists Displaying a Novel Binding Mode", J. Med. Chem., vol. 43, pp. 3614-3623, 2000.
Birch, A.J. et al., "Metabolites of Aspergillus Indicus: The Structure and Some Aspects of the Biosynthesis of Dihydrocanadensolide", Aust. J. Chem., vol. 21, pp. 2775-2784, 1968.
Choo, H-Y et al., "Design and Synthesis of alpha, beta-unsaturated Carbonyl Compounds as Potential ACE Inhibitors", Eur. J. Med. Chem., vol. 35, pp. 643-648, 2000.
Co-pending U.S. Appl. No. 10/148,858, filed Dec. 11, 2000; Inventors: Rajendra Joshi et al.
Co-pending U.S. Appl. No. 10/250,983, filed Jan. 8, 2002; Inventors: Rajendra Joshi et al.
Dethlefsen, L. A. et al., Toxic Effects of Acute Glutathione Depletion by Buthionine Sulfoximine and Dimethylfumarate on Murine Mammary Carcinoma Cells, Radiation Res., vol. 114, pp. 215-224, 1988.
Galpin, I.J. et al., "The Synthesis of an Insulin Active Site Analogue", Tetrahedron, vol. 39(1), pp. 149-158, 1983.
Gasser et al., "Host vs Graft and Graft vs. Host Reactions After Allogeneic Heterotopic Small Bowel Transplantation in the Rat", Transplantation Proc., vol. 24(3), pp. 1128-1129, 1992.
Gerhard, U. et al., "The Free Energy Change of Restricting a Bond Rotation in the Binding of Peptide Analogues to Vancomycin Group Antibiotics", Bioorgan. & Med. Chem. Letters, vol. 3(5), pp. 803-808, 1993.
Gordon, G.B. et al., "Induction of NAD(P)H:quinone reductase in human peripheral blood lymphocytes", Carcinogenesis, vol. 12(12), pp. 2393-2395, 1991.
Griehl, C. et al., "alpha-Aspartyl Peptides by Addition of Amines to N-Malsylamino Acid Derivatives", Chem. Of Peptides and Proteins, vol. 5(6), pp. 99-103, 1993.
Hildebrandt, H., "Pschryembel Klinisches Woerterbuch Ed. 258", Walter de Gruyter, p. 182, col. 1 para. 2, and p. 1469, col. 1 para. 16-col. 2, para. 1, 1998.
Hohenegger, M. et al., "Nephrotoxicity of Fumaric Acid Monoethylester (FA ME)", Adv. In Exp. Med. And Biol., vol. 252, pp. 265-272, 1989.
Holroyd, S.E. et al., "Rational Design and Binding of Modified Cell-Wall Peptides to vancomycin-Group Antibiotic: Factorising Free Energy Contributions to Binding", Tetrahedron, vol. 49(41), pp. 9171-9182, 1993.
Hunziker, T. et al., "Is Psoriasis an Autoimmune Disease?", excerpt from "Therapeutische Umschau", Derm. Clinic of Univ. Berne, vol. 50 (2nd Ed.), pp. 110-113, translated ver. 5 pgs., 1993.
Immun. Durch Fumaderm, das richtungsweise Konzept, Charité-Berlin Symposium 1-3, 28 pages, 4 page translation of pp. 23-24, 1996.

International Search Report for PCT/EP02/00107 dated Aug. 1, 2003 (Priority Application for U.S. Appl. No. 10/433,295).
Kamiyama, T. et al., "Ro 09-1679, A Novel Thrombin Inhibitor", Jour, of Antibiotics, vo. 45(3), pp. 424-427, 1992.
Krstenansky, J.L. et al., "Development of MDL 28,050, a Small Stable Antithrombin Agent Based on a Functional Domain of the Leech Protein, Hirudin", Thrombosis and Haemostasis, vol. 63(2), 1990.
Kuroda, K. et al., "Fumaric Acid Enhances DNA Synthesis of Rat Hepatocytes by Counter Acting the Toxicities of Mitomycin C and Aflatoxin B", Jpn. J. Cancer Res., vol. 77, pp. 750-758, 1986.
Kuroda, K. et al., "Inhibitory Effect of capsella-bursa-pastoris Extract ion Growth of Ehrlich Solid Tumor in Mice", Cancer Research, vol. 36, Abstract only, 1976.
Langlois, M. et al., "Synthesis of symmetrical pseudopeptides as potential inhibitors of the human immunodeficiency virus-I protease", Eur. J. Med. Chem., vol. 29, pp. 639-647, 1994.
Lehnert, S. et al., "Radiation response of Drug-Resistant Variants of a Human Breast Cancer Cell Line: The Effect of Glutathione Depletion", Radiation Research, vol. 142, pp. 208-215, 1990.
Merck Manual, Merck XP-002141006, p. 327, para. 2-para. 6, 1987.
Miller, A.C. et al., "Posttranscriptional Down-Regulation of ras Oncogene Expression by Inhibitors of Cellular Glutathione", Mol. And Cell. Biol., vol. 13(7), pp. 4416-4422, 1993.
Mrowietz, U., "Nephrotoxische Wirkung durch Fumarsauere", Hautartzt, vol. 51, p. 615, 2000.
Murthy, K. et al., J. Pharm. Sci. 82(2): 113-126 (1993).
Nathens et al., "The Glutathione Depleting Agent Diethylmaleate Prolongs Real Allograft Survival", J. Surgical Res., vol. 77, pp. 75-79, 1998.
Nibbering, P.H. et al., "Intracellular Signalling by Binding Sites for the Antipsoriatic Agent Monomethylfumarate on Human Granulocytes", British J. Derm., vol. 137, pp. 65-75, 1997.
Nibbering, P.H., "Effects of Monomethylfumarate on Human Granulocytes", J. Investigative Derm., vol. 101, pp. 37-42, 1993.
Ockenfels, H. M. et al., "The antipsoriatic agent dimethylfumarate immunomodulates T-cell cytokine secretion and inhibits cytokines of the psoriatic cytokine network", British J. Derm., vol. 139, pp. 390-395, 1998.
Odom, R.Y. et al., "Cancer Chemoprotective Agents Inhibition of Human HT29 Colon Carcinoma Cell Proliferation is Reversed by N-Acetyl Cysteine", Proc. of the Amer. Assoc. Cancer Res. Annual, No. 41, p. 342, 2000.
Ondrus, V. et al., "A Simple Synthesis of Some Analogues of Natural Antibiotics", Prelim. Comm., Chem. Papers, vol. 51(3), pp. 164-166, 1997.
Orta, T. et al., "Glutathione manipulation and the radiosensitivity of human tumour and fibroblast cell lines", Int. J. Radiat. Biol., vol. 68(4), pp. 413-419, 1995.
Pearl, J.M. et al., "Fumarate-enriched blood cardioplegia results in complete functional recovery of immature myocardium", Annals of Thoracic Surgery, vol. 57(6), Abstract only, 1 pg., 1994.
Peeters, A.J., "Fumaric Acid Therapy for Psoriatic Arthritis. A Randomized, Double Blind, Placebo-controlled Study", Brit. Jour. Of Rheumatology, vol. XXXI(7), pp. 502-504, 1992.
Pereira, M.A. et al., "Use of azoxymethane-induced foci of aberrant crypts in rat colon to identify potential cancer chemopreventive agents", Carcinogenesis, vol. 15(5), pp. 1049-1054, 1994.
Portoghese, P.S. et al., "Synthesis and Biological Activity of Analogues of beta-Chlornaltrexamineand beta-Funaltrexamine at Opioid Receptors", J. of Med. Chem., vol. 29(10), pp. 1861-1864, 1986.
Prochaska, H.J. et al, "Elevation of Glutathione Levels by Phase II Enzyme Inducers: Lack of Inhibition of Human Immunodeficiency Virus Type I Replication in Chronically infected Monocytoid Cells". Mol. Pharm., vol. 45, pp. 916-921, 1994.
Prochaska, H.J. et al, "Oltipraz, an inhibitor of human immunodeficiency virus type 1 replication", Proc. Natl. Sci., USA, vol. 90, pp. 3953-3957, 1993.
Rao, C.V. et al., "Chemoprevention of Azoxymethane-Induced Colon Cancer by Ascorbylpalmitate, Carbenoxolone, Dimethylfumarate, and p-Methoxyphenol in Male F344 Rates", Anticancer Research, vol. 15, pp. 1199-1204, 1995.

Rao, K.S., "Antihepatoxic activity of monomethylfumarate isolated from Fumaria indica", Jour. Of Ethnopharm., vol. 60, pp. 207-213, 1998.

Roodnat, J.I. Et al., "Akute Niereninsuffienz bei der Behandlung der Psioriais mit Fumarsauere-Estern", Schweiz. Med., vol. 119(2), pp. 826-830, 1989.

Rossi, D. et al. "Approach to the Use of Benzylpenicillinacylase for Configurational Correlations of Amino Compounds. 2. Hydrolysis of N-(p-Aminophenylacetyl) Derivatives of Some Chiral Primary Amines", J. Org. Chem., vol. 44(13), pp. 2222-2225, 1979.

Schirmeister, T., "Aziridine-2, 3-dicarboxylic Acid Derivatives as Inhibitors of Papain", Arch. Pharm. Med. Chem., vol. 329, pp. 239-244, 1996.

Schmidt, K.N. et al., "Anti-psoriatic drug anthralin activates transcription factor NF-kappa-B in murine keratinocytes", Jour. Of Immunology, vol. 156, abstract only, 1996.

Schwinghammer, T. et al., "Pharmacologic prophylaxis of caute graft-versus-host disease after allogeneic marrow transplantation", Therapy Rev., Clinical Pharm., vol. 12, pp. 736-761, 1993.

Sebok, B. et al., "Antiproliferative and Cytotoxic Profiles of Antipsoriatic Fumaric acid derivatives in Keratinocyte Cultures", Euro. J. of Pharm. Environ. Toxicol. Pharmacol. Sect., vol. 270, pp. 79-87, 1994.

Spencer, S.R. et al., "Induction of Glutathione Transferases and NAD(P)H:Quinone Reductase by Fumaric Acid Derivatives in Rodent Cells and Tissues", Cancer Research, vol. 50, pp. 7871-7875, 1990.

Steele, V.E. et al., "Preclinical Efficacy Evaluation of Potential Chemopreventive Drug Development Program", Jour. of Cellular Biochem., Suppl. 20, pp. 32-54, 1994.

Su, J.Y.C. et al., "Reduction of H2O2-evoked, intracellular calcium increases in the rat N18-RE-105 neuronal cell line by pretreatment with an electrophilic antioxidant inducer", Neuroscience Letters, vol. 23, pp. 109-112, 1999.

Subasinghe, N. et al., "Synthesis of Acyclic and Dehydroaspartic Acid Analogues of Ac-Asp-Glu-OH and their Inhibition of Rat Brain N-Acetylated alpha-linked Acidic Dipeptidase (NAALA Dipeptidase)", Jour. Of Med. Chem., vol. 33, pp. 124-130, 2001.

Vandermeeren, M. et al., "Dimethylfumarate is an Inhibitor of Cytokine-Induced E-Selection, VCAM-1, and ICAM-1 Expression in Human Endothelial Cells", Biochem. And Biophys. Res. Com., vol. 234, pp. 19-23, 1997.

Vandermeeren, M. et al., "Dimethylfumarate is an Inhibitor of Cytokine-Induced Nuclear Translocation of Nf-kB1, but not RelA in Normal Human Dermal Fibroblast Cells", The Jour. of Investigative Derm., vol. 116(1), pp. 124-130, 2001.

Wang, X. et al., "Enhanced cytotoxicity of mitomycin C in human tumour cells with inducers of DT-diaphorase", Brit. Jour. of Cancer, vol. 80(8), pp. 1223-1230, 1997.

Weinmann, I. et al., "Influence of Fumaric Acid derivatives on T Lymphocytes in the Murine Model of HSV-I Keratitis", IOVS, vol. 41(4), pp. S146, 2000.

English language abstract of EP 103 274.

H. Werbin et al., "Cyclization of N-Succinylglycine Dimethyl Ester," J. Am. Chem. Soc. 69:1681-1684 (Jul. 1947).

N. Subasinghe et al., "Synthesis of Acyclic and Dehydroaspartic Acid Analogues of Ac-Asp-Glu-OH and Their Inhibition of Rat Brain N-Acetylated α-Linked Acidic Dipeptidase (NAALA Dipeptidase)," J. Med. Chem. 33:2734-2744 (1990).

* cited by examiner

FUMARIC ACID AMIDES

REFERENCE TO RELATED APPLICATIONS

This is a Division of commonly-owned application Ser. No. 10/433,295, filed Jun. 2, 2003, now U.S. Pat. No. 7,157,423, issued Jan. 1, 2007, which turn is a 371 continuation of PCT Application PCT/EP02/00107, filed Jan. 8, 2002.

TECHNICAL FIELD

The present invention relates to certain fumaric acid mono- and diamides, or monoamido fumaric acid monoesters, respectively, as well as the use of such compounds for preparing a drug and drugs containing said compounds.

BACKGROUND

For a long time, fumaric acid dialkyl esters as well as fumaric acid monoalkyl esters and salts thereof have been successfully used for treating psoriasis. Said use is described in a number of patents, for example EP-A-0 188 749, DE-25 30 327, DE 26 21 214 or EP-B-0 312 697.

The use of fumaric acid mono- or diesters is also described for the treatment of autoimmune diseases such as polyarthritis, multiple sclerosis (cf. DE 197 21 099.6 and DE 198 53 487.6), but also for use in transplantation medicine (cf. DE 198 53 487.6 and DE 198 39 566.3). The use of fumaric acid mono- and diesters for the treatment of NF-kappaB mediated diseases and the treatment of mitochondrial diseases is also known from the unpublished German applications DE 101 01 307.8 and DE 100 00 577.2. However, all the cited documents merely describe fumaric acid mono- and diesters, optionally in the form of certain salts, i.e. compounds wherein one or both acid functions of the fumaric acid are esterified with an alcohol.

Because of their volatility and sublimability, however, the above-mentioned fumaric acid esters have the disadvantage of being difficult to handle when preparing pharmaceutical products, especially those in solid form for oral administration. Specifically the preparation of such products requires protective measures such as the use of breathing masks, gloves, protective clothing.

In addition, the fumaric acid esters are absorbed in the gastro-intestinal tract after oral administration and taken up unspecifically from the bloodstream by all body cells. Therefore, it is necessary to administer high dosages in order to provide a therapeutically effective level of the active ingredient on or in the target cells.

Such high dosages in turn lead to the known side effects of a fumaric acid therapy like flush symptoms (reddening) or gastrointestinal irritation (nausea, diarrhea, winds). Even though such side effects may be reduced considerably by administering the active ingredient in the form of microtablets as described in the above-cited prior art, they cannot be avoided altogether.

At the same time, the fumaric acid esters are rapidly hydrolysed in the blood and the products of said hydrolysis, alcohol and fumaric acid or fumaric acid mono ester, metabolised. In order to maintain therapeutically effective levels repeated and frequent administration is therefore necessary. Even though a certain adaptation is observed concerning the side effects, a further reduction of the side effect rate would be desirable.

BRIEF SUMMARY OF THE INVENTION

Therefore, it is an object of the present invention to provide fumaric acid derivatives, which may be administered strategically, are more resistant to hydrolysis and easier to handle, and the use of such derivatives.

The present object is achieved by certain fumaric acid mono- and diamides or monoamido fumaric acid monoesters, respectively, the use thereof for preparing drugs for the therapy of certain diseases and drugs containing the same.

FURTHER DETAILED DESCRIPTION OF THE INVENTION

Fumaric acid diamides and monoamides have also been described in U.S. Pat. No. 5,242,905 and U.S. Pat. No. 5,214,196 to Blank for the treatment of psoriasis. However, these cited publications merely describe the preparation of single fumaric acid mono- or diamides, but not the preparation of pharmaceutical products and the application of the amides on human beings. A theoretical advantage of the fumaric amides over the fumaric acid esters cited by the above publications is the provision of certain amino acids from the fumaric amides in the keratinocytes in order to complement metabolic deficiencies in psoriasis.

Surprisingly, the inventors have now found that the fumaric acid mono- and diamides or monoamido fumaric acid monoesters may be used advantageously for the therapy of a variety of diseases. Specifically, the first aspect of the present invention therefore relates to the use of fumaric acid amides of the general formula (I)

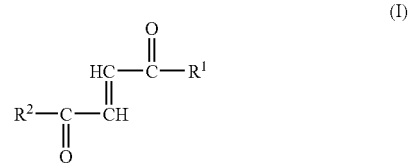

wherein $R^1$ represents $OR^3$ or a D- or L-amino acid radical —NH—$CHR^4$—COOH bonded via an amide bond, wherein $R^3$ is hydrogen, a straight-chained or branched, optionally substituted $C_{1-24}$ alkyl radical, preferably a $C_{1-6}$ alkyl radical, a phenyl radical or $C_{6-10}$ aralkyl radical and $R^4$ is a side chain of a natural or synthetic amino acid and $R^2$ represents a D- or L-amino acid radical —NH—$CHR^5$—COOH bonded via an amide bond or a peptide radical comprising 2 to 100, preferably 2 to 30 amino acids bonded via an amide bond, wherein $R^5$ is a side chain of a natural or synthetic amino acid, for preparing a drug (1) for the therapy of an autoimmune disease selected from the group consisting of polyarthritis, especially rheumatoid arthritis, multiple sclerosis, graft-versus-host reactions, juvenile-onset diabetes, Hashimoto's thyroiditis, Grave's disease, systemic Lupus erythematodes (SLE), Sjogren's syndrome, pernicious anaemia and chronic active (=lupoid) hepatitis;

(2) for use in transplantation medicine (Host-versus-graft-reactions);

(3) for the therapy of mitochondrial diseases selected from the group consisting of Parkinson syndrome, Alzheimer's disease, Chorea Huntington disease, retinopathia pigmentosa or forms of mitochondrial encephalomyopathy; as well as (4) for the therapy of NF-kappaB mediated diseases selected from the group consisting of progressive systemic sclerodermia, osteochondritis syphilitica (Wegener's disease), cutis marmorata (*livedo reticularis*), Behcet disease, panarteriitis, colitis ulcerosa, vasculitis, osteoarthritis, gout, arteriosclerosis, Reiter's disease, pulmonary granulomatosis, types of encephalitis, endotoxic shock (septic-toxic shock), sepsis, pneumonia, encephalomyelitis, anorexia nervosa, hepatitis (acute hepatitis, chronic hepatitis, toxic hepatitis, alcohol-induced hepatitis, viral hepatitis, jaundice, liver insufficiency and cytomegaloviral hepatitis), Rennert T-lymphomatosis, mesangial nephritis, post-angioplastic restenosis, reperfusion syndrome, cytomegaloviral retinopathy, adenoviral diseases such as adenoviral colds, adenoviral pharyngoconjunctival fever and adenoviral ophthalmia, AIDS, Guillain-Barré syndrome, post-herpetic or post-zoster neuralgia, inflammatory demyelinising polyneuropathy, mononeuropathia multiplex, mucoviscidosis, Bechterew's disease, Barett oesophagus, EBV (Epstein-Barr virus) infection, cardiac remodeling, interstitial cystitis, diabetes mellitus type II, human tumour radiosensitisation, multi-resistance of malignant cells to chemotherapeutic agents (multidrug resistance in chemotherapy), granuloma annulare and cancers such as mamma carcinoma, colon carcinoma, melanoma, primary liver cell carcinoma, adenocarcinoma, kaposi's sarcoma, prostate carcinoma, leukaemia such as acute myeloid leukaemia, multiple myeloma (plasmocytoma), Burkitt lymphoma and Castleman tumour.

In a second aspect, the present invention relates to fumaric acid amides of the formula (I)

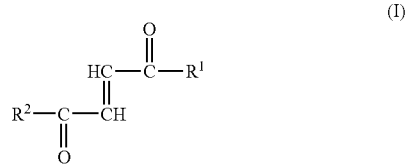

wherein
R¹ represents OR³ or a D- or L-amino acid radical —NH—CHR⁴—COOH bonded via an amide bond, wherein R³ is hydrogen, a straight-chained or branched, optionally substituted $C_{1-24}$ alkyl radical, preferably a $C_{1-6}$ alkyl radical, a phenyl radical or $C_{6-10}$ aralkyl radical and R⁴ is a side chain of a natural or synthetic amino acid and
R² represents a D- or L-amino acid radical —NH—CHR⁵—COOH bonded via an amide bond or a peptide radical comprising 2 to 100 amino acids, preferably 2 to 30 amino acids bonded via an amide bond, wherein R⁵ is a side chain of a natural or synthetic amino acid, with the proviso that
when R³ =H, R², is a peptide radical selected from the group consisting of peptide hormones, growth factors, cytokines, neurotransmitters, neuropeptides, antibody fragments, coagulation factors and cyclosporines as well as derivatives and fragments thereof and
when R¹=—NH—CHR⁴—COOH, R² is a peptide radical selected from the group consisting of peptide hormones, growth factors, cytokines, neurotransmitters, neuropeptides, antibody fragments, cyclosporines and coagulation factors as well as derivatives and fragments thereof, or represents —NH—CHR⁵—COOH wherein R⁵ is selected from the group consisting of the side chains of Ala, Val, Leu, Trp, Phe, Met, Tyr, Thr, Cys, Asn, Gln, Asp, Glu, Lys, Arg, His, Citrullin, Hcy, Hse, Hyp, Hyl, Orn, Sar and Me-Gly.

The term "side chain of a natural or synthetic amino acid" means the radicals of each natural or synthetic amino acid positioned on the α-carbon atom. The amino acid radicals R¹ and R² may be present in the D- and the L-configuration, the natural L-configuration being preferred. Below, the customary abbreviations and designations in the 3-letter code are used to characterise the amino acids.

According to one embodiment, especially compounds of the formula (I) are used and claimed, respectively, wherein R¹ represents —NH—CHR⁴—COOH, and R² rep resents —NH—CHR⁵—COOH, wherein R⁴ and R⁵ may be the same or different and are as defined above. More preferably, R⁴ and R⁵ are independently selected from the group consisting of the side chains of Ala, Val, Leu, Trp, Phe, Met, Tyr, Thr, Cys, Asn, Gln, Asp, Glu, Lys, Arg, His, Citrullin, Hcy, Hse, Hyp, Hyl, Orn, Sar and Me-Gly.

According to another embodiment, compounds of the formula (I) are used or claimed, respectively, wherein R¹ represents —OR³ and R² represents an L-amino acid radical —NH—CHR⁵—COOH, wherein R⁵ is selected from the group consisting of the side chains of Ala, Val, Leu, Trp, Phe, Met, Tyr, Thr, Cys, Asn, Gln, Asp, Glu, Lys, Arg, His, Citrullin, Hcy, Hse, Hyp, Hyl, Orn, Sar and Me-Gly.

Especially preferably R⁵ is a polar amino acid in both embodiments, even more preferably a charge-bearing amino acid selected from the group consisting of asparagine, glutamine, lysine, arginine and histidine.

When the radical R¹ represents —OR³, i.e. when the compound of the formula (I) to be used according to the invention or claimed, respectively, is a monoamido fumaric acid monoester or monoamide, R³ is preferably selected from the group consisting of a linear, branched, cyclic, saturated or unsaturated $C_{1-24}$ alkyl radical, preferably a $C_{1-6}$ alkyl radical, a phenyl radical or a $C_{6-10}$ aralkyl radical and this radical is optionally substituted with halogen (F, Cl, Br, I), hydroxy, $C_{1-4}$ alkoxy, nitro or cyano. Preferably R³ is methyl, ethyl, n-propyl, isopropyl, n-butyl, sec-butyl, t-butyl, pentyl, cyclopentyl, 2-ethylhexyl, hexyl, cyclohexyl, heptyl, cycloheptyl, octyl, vinyl, allyl, 2-hydroxyethyl, 2- or 3-hydroxypropyl, 2,3-dihydroxypropyl, 2-methoxyethyl, methoxymethyl or 2- or 3-methoxypropyl. Most preferably R³ is methyl or ethyl.

According to another embodiment of the invention, compounds of the formula (I) are used wherein R¹ represents —OR³, preferably with R³=methyl or ethyl, and R² represents a peptide radical with 2 to 100, preferably 2 to 30 amino and most preferably 5 to 25 amino acids bonded via an amide bond. Said peptide radical may be a natural, recombinant or synthetic peptide radical.

More preferably, the peptide radical R², is selected from the group consisting of peptide hormones, growth factors, cytokines, neurotransmitters, neuropeptides, antibody fragments, coagulation factors and cyclosporines as well as derivatives and fragments thereof. Said peptides may be purified from natural sources, recovered by recombinant methods or synthesised in accordance with known processes. The use of synthetic peptides is preferred.

Coupling the fumaric acid body to such a functional peptide has the advantage of the peptide providing a transmission of the active ingredient "fumaric acid body" to target cells with which the peptide portion of the amides of the invention interacts. At the same time, the peptide portion may have its own effect on the disease to be treated so that a combination therapy is effected in this case. However, a combination therapy and/or strategic administration permit reduction of the dose to be administered in a desirable, possibly even synergistic manner.

According to a preferred embodiment of the invention, the peptide radical may be a cyclosporine radical the cycle of which may be cleaved at each peptide bond in order to enter into the fumaric acid amide bonding. In general, all cyclosporines may be bonded to the fumaric acid body by an amide bond in the invention. Since cyclosporines are cyclic peptides, the peptide ring is generally cleaved at any position (at any amide bond) in order to obtain a linearised cyclosporine capable of entering into an amide bond. Preferably cyclosporine A linearised before position 1 is used.

The term "peptide hormones" as used here means physiologically highly active peptides with approximately up to 100 amino acids which develop a hormone effect or hormone-like effect. Examples are the glandular peptide hormones of the pituitary gland such as corticotropin, follitropin, lutropin, melanotropin, prolactin, somatotropin, thyrotropin, oxytocin and vasopressin, the releasing hormones and inhibiting factors of the hypothalamus, the peptide hormones from the pancreas, stomach or intestine such as glucagon, insulin, somatostatin, sectretin, gastrin and cholecystokinin, the peptide hormones of the thyroid such as calcitonin, parathyrin and such like.

The term "growth factors" means hormone-like peptides and proteins which support cell division and cell differentiation, promote growth and organ development and are needed for wound healing. Examples are colony-stimulating factors, the epidermal growth factor (EGF), erythropoietin, fibroblast growth factors, haematopoietic growth factors, hepatocyte growth factors, insulin and insulin-like growth factors, the platelet-derived growth factor (PDGF), thrombopoietin, transforming growth factors, viral growth factors, but the interleukins, too.

The term "cytokines" as used in the present application refers to polypeptides which are secreted by cells and, after bonding with specific receptors, may influence the function of other, usually adjacent cells. Cytokines primarily regulate the complex interaction of the cells of the immune system. Examples of such cytokines are interferons, interleukins, chemokines or colony-stimulating factors.

The term "neurotransmitter" means messenger substances which effect the chemical signal or information transmission on the synapses of the nervous system. Depending on their chemical characteristics, neurotransmitters are divided into amino acids such as glutamine acid, amino acid derivatives such as acetylcholine, monoamines like the catechol amines, such as L-noradrenalin, L-adrenalin and dopamine, serotonin and peptides. Accordingly, the "neuropeptides" like bradykinin, but also the enkephalines, endorphin etc. are a sub-group of the neurotransmitters.

The term "coagulation factors" as used here means proteins of the coagulation cascade. Likewise, the peptide which, in the invention, may be coupled to the fumaric acid via an amide-bonding may be an antibody fragment, said fragment preferably also comprising a recognition sequence and/or bonding sequence.

Fragments and/or derivatives of all the peptides enumerated above which are suitable for the invention may also be used. The term "fragment" means a portion of the above-mentioned peptides which is capable of amide bonding. Preferably, said fragment comprises recognition sequences for arranging bonding to a cell receptor and/or an active centre for transmitting an active function.

The term "derivative" means a peptide which may be derived from the above-mentioned peptides and/or fragments by homologous substitution, deletion or insertion of one or more amino acid(s) into or from the peptide chains.

The fumaric acid amides of the invention may be prepared in accordance with the above-mentioned U.S. patents to Blank.

In a third aspect, the present invention relates to drugs comprising a fumaric acid amide as defined above or mixtures thereof. The drugs obtained through the use according to the invention and/or through the use of the claimed fumaric acid amides may be present in forms suitable for oral, nasal, parenteral, rectal, pulmonal, ophthal or transdermal administration.

Preferably, the drug is intended for oral administration and is present in the form of tablets, coated tablets, capsules, granulate, solutions for drinking, liposomes, nano-capsules, micro-capsules, micro-tablets, pellets or powders as well as granulate, micro-tablets, pellets and powder filled in capsules, micro-tablets filled in capsules and powder filled in capsules.

According to a particularly preferred embodiment, the drug is a solid oral dosage form and, even more preferably, has an enteric coating (coating resistant to gastric acid). For example such a coating may be provided on tablets, coated tablets, micro-tablets, pellets or capsules.

As a matter of principle, the drug of the invention may contain suitable pharmaceutically acceptable carriers, excipients, additives etc. These are known to the person skilled in the art and do not require an explanation.

The use of micro-tablets or pellets is most preferred. Preferably, these have a mean diameter of 300 to 5000 μm, more preferably 300 to 2000 μm, when uncoated.

When administered parenterally by injection, the composition is present in a form suitable for this purpose. All customary liquid carriers suitable for injection may be used.

In any case, it is preferred that a single dose of the drug contains an amount of the fumaric acid amide of the formula (I) which corresponds or is equivalent to an amount of 1 to 500 mg, preferably 10 to 300 mg and most preferably 10 to 200 mg of fumaric acid.

That which is claimed is:

1. A fumaric acid amide formula

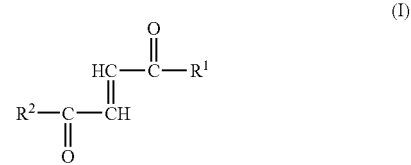

wherein:
$R^1$ is —$OR^3$;
$R^2$ is a peptide radical comprising 5 to 25 amino acids wherein the N-terminus of the peptide radical is bonded via an amide bond to a second carboxyl carbonyl of the fumaric acid, wherein the peptide radical is other than (i) a cyclosporine radical or (ii) a cyclosporine linearised at any amino acid position in the cyclosporine ring; and
$R^3$ is a straight-chained $C_{1-24}$ alkyl radical, cyclic $C_{1-24}$ alkyl radical, branched $C_{1-24}$ alkyl radical, phenyl radical or $C_{6-10}$ aralkyl radical, each of which is optionally substituted.

2. The fumaric acid amide according to claim 1 wherein, $R^2$ is a peptide hormone, growth factor, cytokine, neurotransmitter, neuropeptide, antibody fragment, coagulation factor or a fragment thereof.

3. The fumaric acid amide of claim 1, wherein $R^3$ is methyl or ethyl.

4. The fumaric acid amide of claim 1, wherein $R^3$ is a $C_{1-24}$ alkyl radical, cyclic $C_{1-24}$ alkyl radical, branched $C_{1-24}$ alkyl radical, phenyl radical or $C_{6-10}$ aralkyl radical, each of which is optionally substituted with halogen, hydroxy, $C_{1-4}$ alkoxy, nitro or cyano.

5. The fumaric acid amide of claim 1, wherein $R^3$ is methyl, ethyl, n-propyl, isopropyl, n-butyl, sec-butyl, t-butyl, pentyl, cyclopentyl, 2-ethylhexyl, hexyl, cyclohexyl, heptyl, cycloheptyl, octyl, vinyl, allyl, 2-hydroxyethyl, 2-hydroxypropyl, 3-hydroxypropyl, 2-methoxyethyl, 2,3-dihydroxypropyl, methoxymethyl, 2-methoxypropyl or 3-methoxypropyl.

6. A pharmaceutical composition comprising the fumaric acid amide of claim 1 and at least one excipient or carrier.

7. The pharmaceutical composition according to claim 6 wherein the composition is in a form suitable for oral, nasal, parenteral, rectal, pulmonary, ophthalmic or transdermal administration.

8. The pharmaceutical composition according to claim 6, said composition being adapted for oral administration and being (i) in the form of tablets, coated tablets, capsules, granulate, solutions for drinking, liposomes, nanocapsules, microcapsulles, microtablets, pellets or powders; or (ii) in the form of capsules filled with granulate, microtablets, pellets or powder.

9. The pharmaceutical composition according to claim 8, said product being a solid oral dosage form and having an enteric coating.

10. The pharmaceutical composition according to claim 8 wherein the microtablets or pellets without coating have a mean diameter of 300 to 5000 μm.

11. The pharmaceutical composition according to claim 8, wherein the microtablets or pellets without coating have a mean diameter of 300 to 2000 μm.

12. The pharmaceutical composition according to claim 6, said composition containing an amount of the fumaric acid amide of formula (I) per single dose which corresponds to 1 to 500 mg of fumaric acid.

* * * * *

UNITED STATES PATENT AND TRADEMARK OFFICE
CERTIFICATE OF CORRECTION

PATENT NO. : 7,432,240 B2
APPLICATION NO. : 11/421083
DATED : October 7, 2008
INVENTOR(S) : Rajendra Kumar Joshi et al.

Page 1 of 1

It is certified that error appears in the above-identified patent and that said Letters Patent is hereby corrected as shown below:

Claim 8, col. 8, line 3, "microcapsulles" should read --microcapsules--.

Signed and Sealed this

Twenty-eighth Day of April, 2009

JOHN DOLL
*Acting Director of the United States Patent and Trademark Office*